United States Patent [19]
Adams et al.

[11] Patent Number: 5,937,950
[45] Date of Patent: Aug. 17, 1999

[54] CABLE SYSTEM FOR MEDICAL EQUIPMENT

[75] Inventors: Theodore Robert Adams, Amlin; Glenn D. Brunner, Dublin; James Finley, Columbus, all of Ohio

[73] Assignee: Medex, Inc., Dublin, Ohio

[21] Appl. No.: 08/759,298

[22] Filed: Dec. 2, 1996

[51] Int. Cl.⁶ ............................................. H01B 17/00
[52] U.S. Cl. .................... 172/72 R; 439/502; 248/63; 248/224.51
[58] Field of Search ................. 174/70 R, 71 R, 174/72 R, 72 A, 135; 439/502, 505, 506, 623; 248/63, 224.51; 128/DIG. 26

[56] References Cited

U.S. PATENT DOCUMENTS

| | | | |
|---|---|---|---|
| 3,487,159 | 12/1969 | Jechin | 174/72 R |
| 3,544,060 | 12/1970 | Stoltz | 251/9 |
| 3,776,387 | 12/1973 | Brent | 211/70.6 |
| 3,920,295 | 11/1975 | Speckin | 312/108 |
| 4,211,380 | 7/1980 | Lillegard et al. | 248/229.15 |
| 4,500,150 | 2/1985 | Leibensperger et al. | 439/502 |
| 4,844,249 | 7/1989 | Coulombe | 206/438 |
| 4,844,397 | 7/1989 | Skakoon et al. | 248/231.71 |
| 5,114,023 | 5/1992 | Lavin | 211/107 |
| 5,161,764 | 11/1992 | Roney | 248/231.71 |
| 5,168,124 | 12/1992 | Takase et al. | 174/23 R |
| 5,322,253 | 6/1994 | Stevens | 248/229.15 |
| 5,326,059 | 7/1994 | Pryor et al. | 248/231.71 |
| 5,385,324 | 1/1995 | Pryor et al. | 248/228.3 |
| 5,400,991 | 3/1995 | Werner | 248/230.4 |
| 5,435,448 | 7/1995 | Kempen | 206/370 |

FOREIGN PATENT DOCUMENTS

| | | |
|---|---|---|
| 0 466272 | 1/1992 | European Pat. Off. . |
| 481290 | 4/1992 | European Pat. Off. . |
| 0 603666 | 6/1994 | European Pat. Off. . |
| 715385 | 6/1996 | European Pat. Off. . |
| WO9413197 | 6/1994 | WIPO . |
| WO9701364 | 1/1997 | WIPO . |

*Primary Examiner*—Kristine Kincaid
*Assistant Examiner*—Kamand Cuneo
*Attorney, Agent, or Firm*—Wood, Herron & Evans, L.L.P.

[57] ABSTRACT

A medical cable system includes a plurality of device cables (24) having distal ends adapted to be electrically connected to medical sensing devices (22) that, in turn, are attached to a patient. A main cable (28) has a first end electrically connected to proximal ends of the plurality of device cables (24), and a second end adapted to be connected to a monitor (26). A cable furcation block supports (46) the proximal ends of the device cables (24) and the first end of the main cable (28) with respect to a pole clamp (36). The cable furcation block (46) may be releasably coupled to the mount (36).

15 Claims, 3 Drawing Sheets

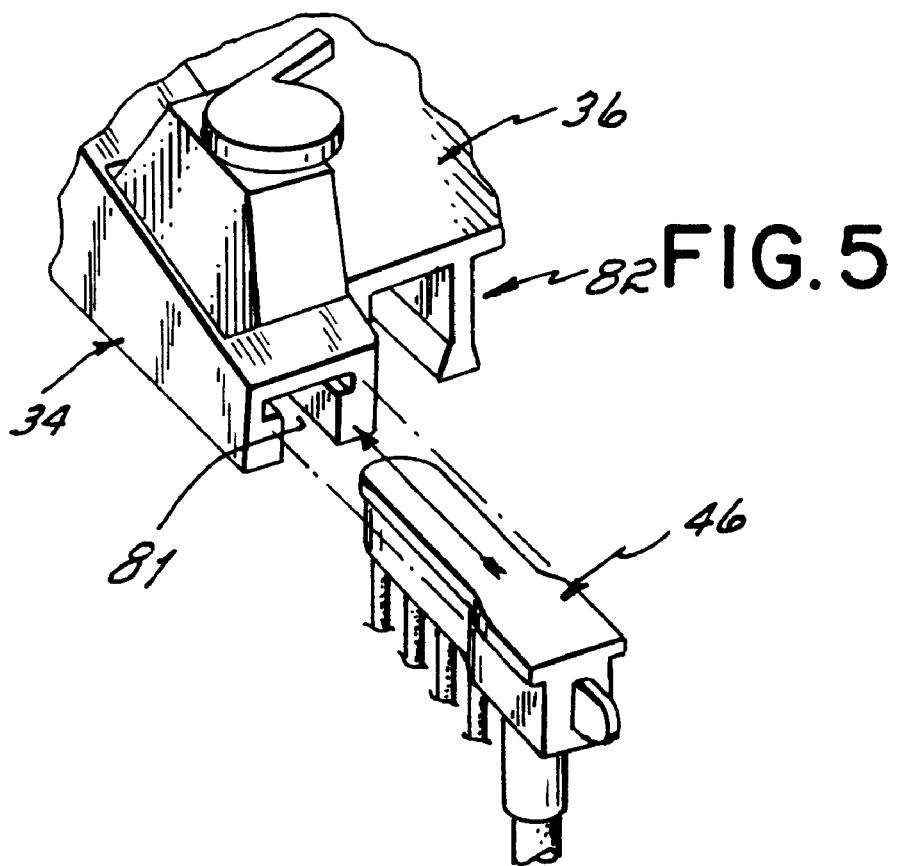

CABLE SYSTEM FOR MEDICAL EQUIPMENT

FIELD OF THE INVENTION

This invention relates generally to medical equipment and more particularly, to an improved cable system for interconnecting sensors with associated monitoring equipment.

BACKGROUND OF THE INVENTION

Improvements in medical care in the hospital or similar environment have resulted in an ever increasing number of patient monitoring devices being used. For example, a patient may have one or more blood pressure sensors, one or more pulse sensors, a thermometer, etc. Normally, such sensors or transducer elements are, in known manner, either mounted at a location close to the patient, attached to the patient or implanted within the patient. Those transducer elements most often provide electrical signals that are carried by cables to one or more monitor devices located either in the patient's room, or at a remote location.

In the process of running the various signal-carrying cables from the respective sensors to the monitor unit device, the cables may be secured to the bed frame, to an IV pole, to hooks extending from the IV pole, and often those cables are bound together with ties or tape. Further, the cables then may be run across an area of the floor to the location of the monitor. With so many cables extending over such a wide area, there is an increased probability that the cables may interfere or be damaged by normal activities associated with the patient. For example, the cables may catch on clothing and otherwise interfere with the activities of the patient or the care giver. In other situations, the cables may present a trip hazard. Further, the cables may be caught up in cleaning equipment or other tools used in the physical maintenance of the room, thereby exposing the cables themselves to damage.

The problem of cable management in the medical care environment is addressed in the European patent publication No. 466 272 A1 in which a plurality of cables carrying electric signals from various sensors are terminated through electrical connectors into a junction box, which, itself, is rigidly mounted to a pole clamp. The signals from the plurality of sensors are consolidated in the junction box into a single output connector and then into one end of a single common cable. At the other end of the common cable, wires are separated from the common cable and connected to their respective monitors. While such a cable system is a significant improvement over running individual cables from the sensors to the monitors, the above described cable system does have several significant disadvantages. For example, often, the least reliable component in an electrical system is any type of mechanical contact required to maintain electrical conductivity. Such mechanical contacts are manifested by the pins and sockets associated with electrical connectors. In a medical care environment, the reliability of mechanical contact between the pins and sockets to maintain electrical conductivity is further reduced by the presence of liquids, both conductive and corrosive. Those liquids can contaminate the mating surfaces between the pins and sockets and interfere with the electrical conductivity through a connector, thereby causing a distortion or interruption of the signal passing through the connector. Consequently, to optimize the reliability of the system, it is desirable to minimize the number of electrical connectors.

Electrical connectors have further disadvantages in that they increase costs, and their physical size is substantially greater than the interconnecting wires they conduct, thereby substantially increasing the size of the device through which the interconnecting wires are to be run. In a medical care environment, larger components consume valuable space, are more difficult to handle, and generally impede the mobility of the device.

With current practices, often, once a patient begins a monitoring process, that monitoring continues with the same devices until monitoring is no longer required. The junction box of the prior art device is rigidly connected to a pole clamp; and therefore, in order to move the junction box from one location to another, the pole must be moved also, or the pole clamp removed from the pole. Often pole clamps are very tightly applied to the poles, and it is not only physically difficult, but time consuming to loosen a screw clamp to provide adequate clearance for the clamp to be removed from the pole. Such time delays are often a hindrance when the patient must be quickly moved from one location to another.

SUMMARY OF THE INVENTION

The present invention provides an improved cable system for a hospital environment that manages the multiplicity of cables connected to plurality of sensors attached to a patient. The cable system of the present invention maintains the cables in an organized manner with a unique support during periods of both use and nonuse. Further, the cable system of the present invention not only consolidates the cables extending between the sensors and the monitor, but also provides that cable consolidation with components that are electrically reliable, compact and low in cost.

To this end and in accordance with the principles of the present invention, the hospital cable system includes a plurality of device cables having distal ends adapted to be electrically connected to medical sensing devices that, in turn, are attached to a patient. The cable system further includes a main cable having a first end electrically connected to proximal ends of the plurality of device cables, and a second end of the main cable is adapted to be connected to a monitor. A cable furcation block supports the proximal ends of the device cables and the first end of the main cable. The cable furcation block is releasably coupled to a mount by cooperating coupling elements on the furcation block and the mount. The mount is further adapted to be attached to a structure such as directly to a pole or to a supporting pole clamp. The cooperative coupling elements facilitate the rapid transportation of the cabling system from one location to another.

In one aspect of the invention, one of the cooperative coupling elements is a slot in the mount having a shape corresponding to a shape of the furcation block to permit the furcation block to slide in and be supported by the mount.

In a further aspect of the invention, the distal ends of the device cables terminate into electrical connectors and the mount further includes a plurality of cavities shaped to receive and support the connectors on the mount. Therefore, placing the electrical connectors on the device cables in the cavities protects the electrical connectors from contamination and damage.

These and other objects and advantages of the present invention will become more readily apparent during the following detailed description taken in conjunction with the drawings herein.

BRIEF DESCRIPTION OF THE DRAWINGS

The accompanying drawings, which are incorporated in and constitute a part of the specification, illustrate embodi

FIG. 5 is a fragmentary perspective view of an alternative embodiment in accordance with the principles of the present invention.

DETAILED DESCRIPTION OF THE INVENTION

Figure 1:
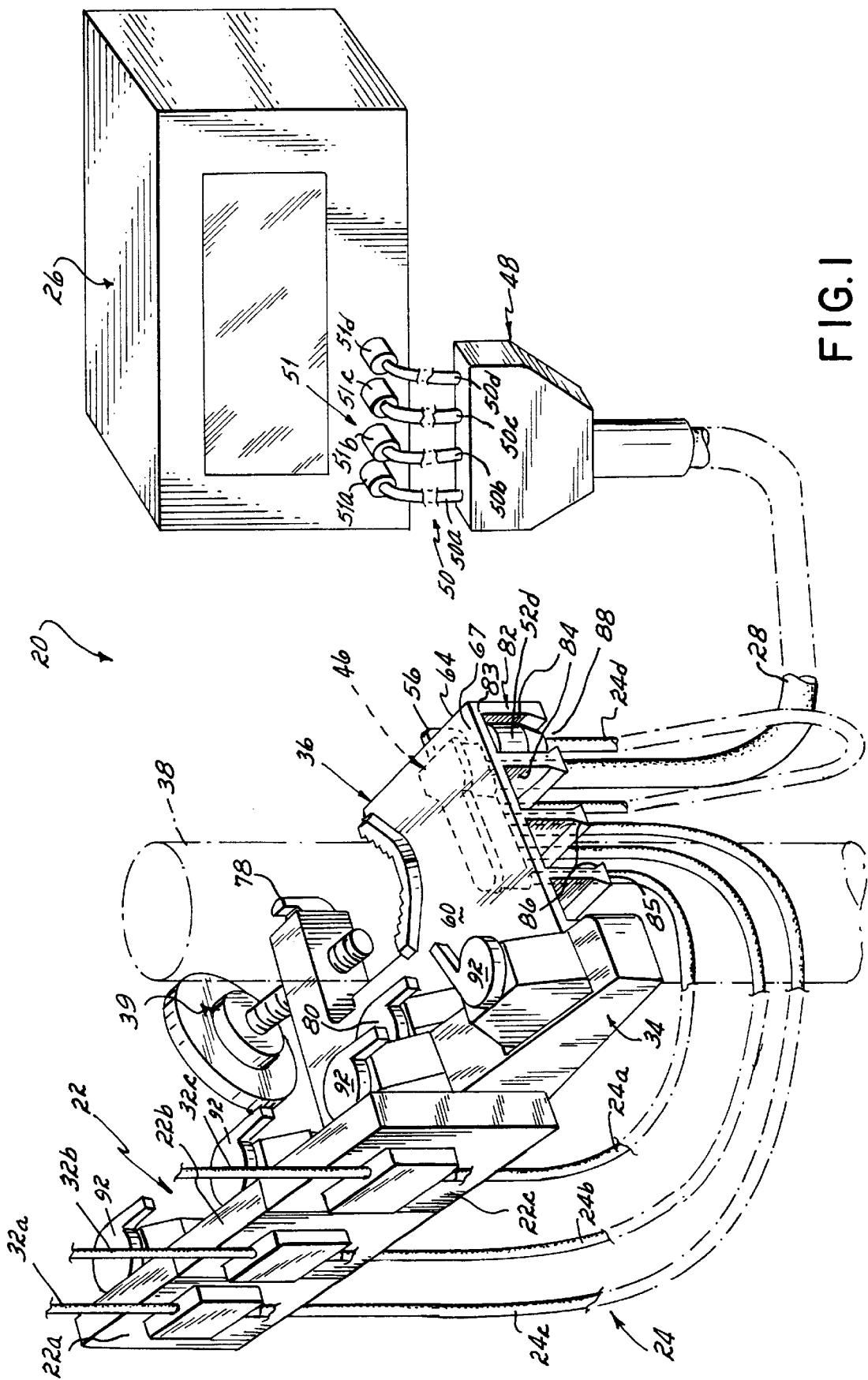
- FIG. 1 is a perspective view of a cabling system interconnected with its associated components in accordance with the principles of the present invention.

Referring to FIG. 1, a medical cabling system 20 permits a plurality of medical devices 22 having individual device cables 24 to be connected to one or more monitor units 26 by a single, main cable 28. The monitor units 26 may be located either in the general vicinity of the patient or at remote locations. The medical devices 22 may be pressure transducers 22a–22c, which are coupled to a patient by means of respective fluid carrying tubes 32a–32c. The pressure transducers 22a–22c are removably mounted on a mounting bracket 34 that, in turn, is mounted to a pole mount or clamp 36. The pole clamp 36 is in turn attached to a structure, for example, pole 38, using a clamp, such as screw clamp 39. The structure for mounting the transducers 22 to the bracket 34 and the bracket 34 to the pole clamp 36 is described in detail in copending U.S. patent application Ser. No. 08/495,923 filed on Jun. 28, 1995 and assigned to the assignee of the present application. The disclosure of the copending U.S. patent application Ser. No. 08/495,923 is hereby incorporated by reference in its entirety. The transducers 22a–22c produce output signals on respective cables 24a–24c each representing a measured pressure, for example, blood pressure.

Normally, the cables 24 extend individually from the transducers 22 to the monitor units 26. As previously described, managing those cables which may extend from 2 to 4 meters or more within the environment of the patient is difficult. The cables not only present unwanted interference, but are subject to damage from inadvertent contact with persons and equipment. The cabling system 20 of the present invention consolidates the cables 24 into a single cable 28 extending between the proximity of the transducers 22a–22c and the monitor unit 26. In accordance with the principles of the present invention, the cables 24 from respective transducers 22 terminate into a first cable furcation block 46 (FIG. 2) mounted within the pole clamp 36. The cables 24a–24d are consolidated within the cable block 46 into the single cable 28. The single cable 28 extends the several meters from the cable block 46 to a second cable furcation block 48. The cable block 48 has individual monitor cables 50 on its output, which are then connected to the one or more monitor units 26. Thus, the consolidated single cable 28 is split into four cables 50a–50d corresponding to the cables 24a–24d, respectively. The distal ends of cables 50a–50d terminate into connectors 51a–51d which, in turn, are connected to mating connectors (not shown) on the monitor 26.

Figure 2:
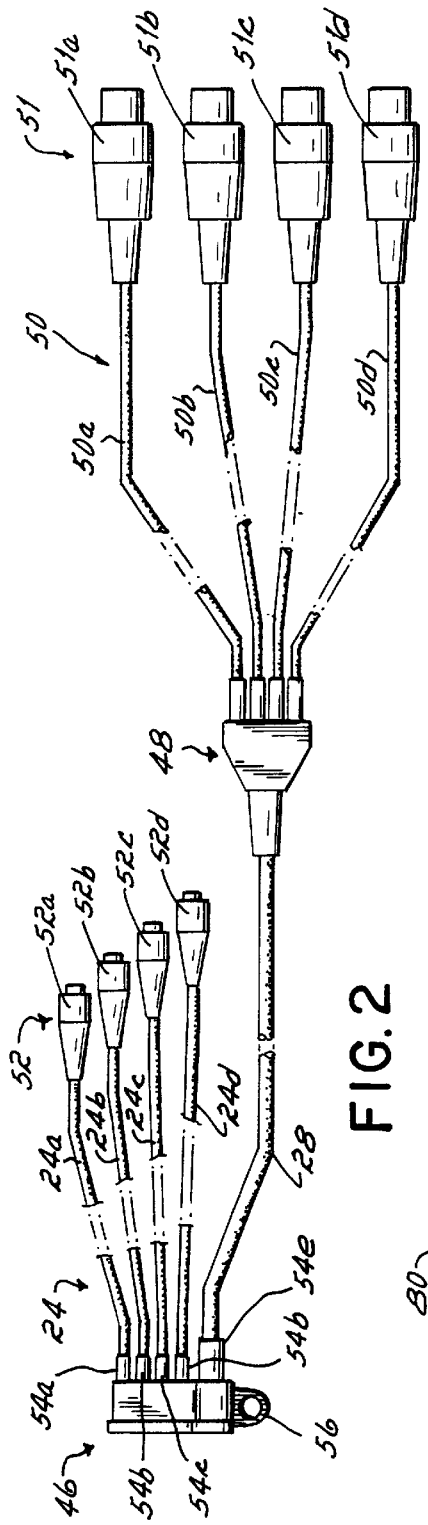
FIG. 2 is a plan view of the cable system of FIG. 1 detached from its associated components.

FIG. 2 illustrates the cable system 20 in more detail. The cables 24a–24d are terminated at their proximal ends into the cable block 46 and the distal ends of cables 24 are terminated with respective connectors 52a–52d, which may be coupled with mating connectors (not shown) located on the lower sides of the respective transducers 22. Each of the cables 24a–24d is a four wire cable with two wires providing an excitation signal to a transducer and the other two wires carrying an output signal from a respective one of the transducers 22. Those four wires are preferably surrounded by a shield, and the shield may include extra conductors to facilitate connecting the shield to the connectors 52. Each of the wires in each of the cables 24a–24d entering the cable furcation block 46 is spliced together with a corresponding wire exiting the cable furcation block 46 in the cable 28. Consequently, the four conductors in each of the cables 24a–24d will result in 16 conductors within the cable 28. Preferably, the conductors carrying the output signals from the transducers 22 are centrally located within the cable 28 and surrounded by a shield. The conductors carrying the excitation signals for the transducers 22 are located peripherally within the cable 28 and also surrounded by a shield. Other ground conductors and/or shields may be included in a known manner.

Cable furcation block 46 is preferably molded in a two step process. The proximal ends of the cable 24 and one end of the cable 28 and their spliced interconnections (not shown), as appropriate, are laid up in a first mold. A mass of plastic, preferably, a lower cost polyethylene, is molded around the proximal ends of the cables 24, 28 to generally form the furcation cable block. That component is then placed in a second mold and a second material, for example, a polyvinyl chloride is molded as a veneer layer around the component to provide the final shape to the cable furcation block 46. Thus the proximal ends of the cables 24 and the one end of the cable 28 are permanently and nonremovably connected to and within the cable furcation block 46. Cable strain relief elements 54a–54e and the finger grip or handle 56 are also formed in the second mold. The process for making the cable furcation block 48 is substantially identical to that just described with respect to cable block 46. The spliced interconnections (not shown) of wires in the proximal ends of cables 50a–50d with respective wires in the opposite end of the main cable 28 are permanently and nonremovably molded into the cable block 48. The distal ends of the cables 50 are terminated with connectors 51a–51d, which are connectable to respective mating connectors (not shown) on the monitor units 26.

Figure 4:
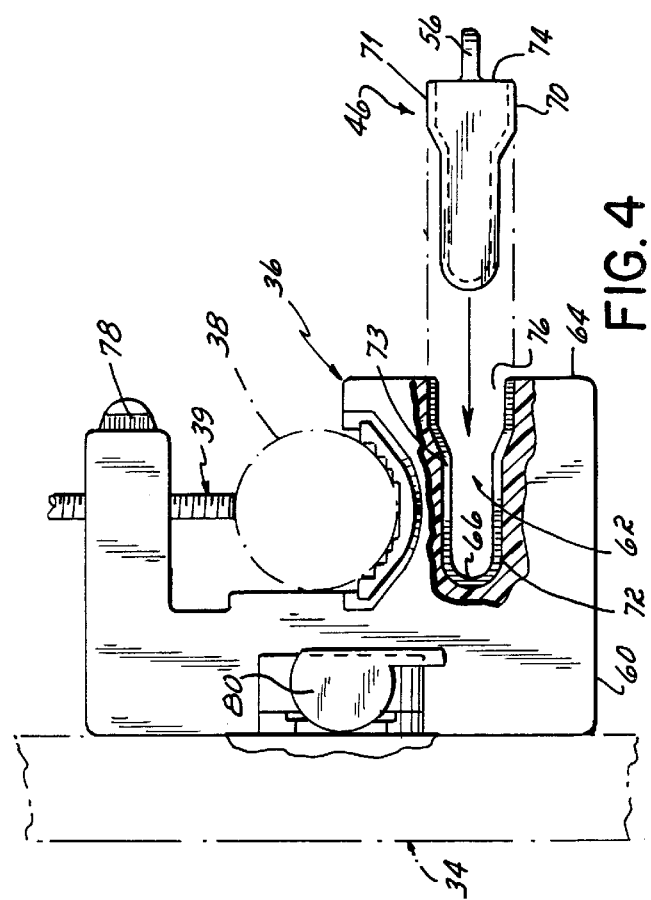
FIG. 4 is a top view of the pole mount of FIG. 3 partially cut away to illustrate profiles taken in a horizontal cross-section of the cable block and the mating slot in the pole mount.
Figure 3:
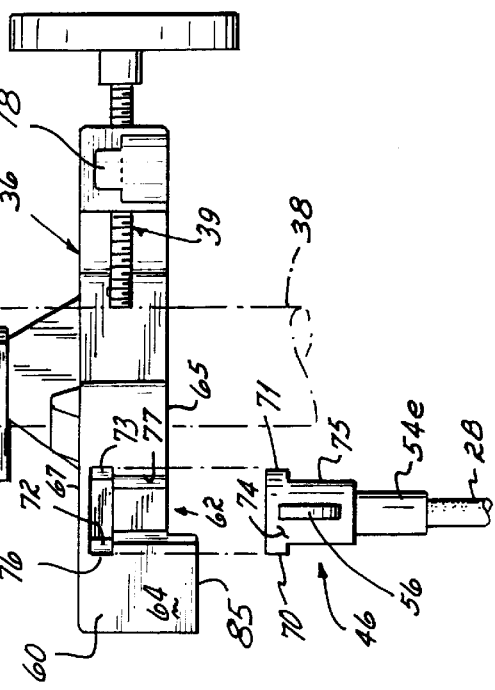
FIG. 3 is a side elevation view of a pole clamp illustrating a vertical cross-sectional profile of a cable block and a mating profile of a slot in a pole mount into which the cable block mounts.

In order to better manage the cable system 20 of FIG. 2, it is preferable that the cable furcation block 46 be located in the proximity of the transducers 22. To that end, as illustrated in FIGS. 3 and 4, the cable furcation block 46 and pole clamp 36 have mating components that permit the cable block 46 to be mounted to the pole clamp 36. More specifically, the body 60 of the pole clamp 36 has a first coupling component or element, for example, a slot 62 that has a generally T-shaped vertical cross-section that preferably is open to a rear side 64 (FIG. 4) and a bottom 65 of the pole clamp 36 (FIG. 3). The slot 62 has a closed end 66 and is covered by an upper portion 67 of the pole clamp 36. The cable block 46 has a second, mating coupling component or element in the form of a vertical cross-sectional profile that is also generally T-shaped with upper lateral flanges or ears 70, 71. The profile of the cable block 46 is shaped to slide into the slot 62 from the rear side 64 of the pole clamp. The cable block 46 has flanges 70, 71 that mate with and slide into horizontally extending slot portions 72, 73 at the upper portion of the slot 62. The flanges 70, 71 and slot portions 72, 73 cooperate to provide a vertical support for the cable block 46 within the pole clamp 36. When the cable block 46 is located within the slot 62, the cables 24, 28 hang vertically downward from the bottom 65 of the pole clamp 36.

As illustrated in FIG. 4, the cable block 46 has a longitudinal profile with a flared larger end 74 to accommodate the larger cable 28. Similarly, the slot 62 in the pole clamp 36 also has a mating flared outer end 76 that accepts the larger end 74 of the cable block 46. Preferably, pole clamp 36 is molded of plastic material such that the pole clamp 36 is chemical resistant, nonbrittle and has a high rigidity with low creep. In addition, preferably, the veneer material molded on the cable block 46 is an elastomeric material, for example, a 60 durometer polyvinyl chloride that produces a softer, pliable, generally resilient texture. Preferably, the sides 75 of the cable block 46 are made to have a slight interference fit with the sides 77 of the slot 62, so that, upon the cable block 46 being inserted into the slot 62, the friction between the elastomeric veneer on the cable block 46 and the sides 77 of the slot 62 functions to prevent the cable block 46 from inadvertently falling out of the slot 62. As will be appreciated, the slot 62 or the cable block 46 may have one or more tapered edges to provide additional interference and support for the cable block 46 in the slot 62. The pole clamp 36 further includes a hook 78 from which fluid bags and other items may be hung.

In use, the pole clamp 36 is attached to the pole 38 at a convenient location. The bracket 34 is mounted on the pole clamp 36 and held in place by latch 80. Thereafter, the grip 56 is used to insert the cable furcation block 46 into the slot 62 of the pole clamp 36 and the soft pliable veneer material on the outer surface of the cable furcation block 46 provides a relatively high friction interface between the slot 62 and the block 46 to more firmly hold the block 46 in the slot 62. When the cable block 46 is hanging in the pole clamp 36, the cables 24, 28 hang down from the bottom of the pole clamp 36 and are readily accessible.

To further manage the cable system 20, mount 36 contains several, such as four, connector storage compartments in the form of cavities 82, which are located in one end 83 of the pole clamp 36 and shaped to receive the connectors 52. The storage cavities 82 have generally straight vertical walls 84 that converge at 86 to provide openings 88 on the bottom 85 of clamp 36 which are sized to receive the cables 24. The storage cavities 82 further have a top area or cover 67 that protect the open end of the connectors 52 from being contaminated with fluids or other debris. Therefore, during the set up procedure, one or more of the connectors 52 may be inserted into a like number of the storage areas 82 on the pole clamp 36 to protect them from contamination or other accidental damage.

In continuing the setup procedure, the transducers 22 are temporarily placed on the bracket 34. The transducers may hang from the bracket without being locked in position so that they may be readily lifted off and placed back on the bracket as they are manipulated during the setup procedure. For example, the transducers may be removed from the bracket to connect a respective hose 32. The transducer may again be placed back on the bracket 34. When one of the cables 24 is to be attached to a respective transducer 22, normally, the transducer 22 is lifted off of the bracket 34, a respective connector 52 is removed from its protective storage location 82 and attached to a mating connector (not shown) the transducer 22. After the transducers 22 have been connected to the other equipment, they may then be secured to the bracket 34 using the latches 92. If for any reason one of the transducers 22 is not being used, its associated connector, for example, connector 52d, is stored in a storage location 82 to minimize the potential for contamination and damage to the connector 52d.

The cabling system 20 described above has the advantages of maximizing the electrical reliability, being compact and light in weight, and having less cost by minimizing the number of electrical connectors. The cable system 20 has the further advantage of flexibility in use. For example, when it is necessary to transport the patient, the entire cabling system may be transported by loosening the screw clamp 39 and disconnecting the pole clamp 36 from the pole 38. Alternatively, that procedure may be too time consuming, or for other reasons, it may be desirable to leave the pole clamp 36 in place. In that situation, the latch 80 is simply moved through an approximately quarter rotation, thereby permitting the bracket 34 to be removed from the pole clamp 36 and using handle 56, the cable furcation block 46 is removed from the pole clamp 36, thereby permitting a quick removal and transportation of the entire cable system 24, 28, 46 with the bracket 34 and medical devices 22. Therefore, the entire cabling system 20 is ready for transport on almost an instantaneous basis. The pole clamp 36 has a plurality of connector storage locations 82 which further enhance the management of the cable system 20 and permit the connectors to be stored, thereby protecting them from physical damage and contamination.

While the present invention has been illustrated by the description of one embodiment, and while that embodiment has been described in considerable detail, it is not the intention to restrict or in any way limit the scope of the appended claims to such detail. Additional advantages will readily appear to those who are skilled in the art. For example, the cabling system 20 described herein utilizes four cables 24 and four cables 50. Alternatively, the cable system 20 may be manufactured to have two or three cables 24 and a corresponding two or three cables 50. While the transducers 22 are described as being pressure sensors, other sensors, for example, pulse, temperature, etc., may be used.

The cable block 46 is removably attached to the pole clamp 36 by sliding into a slot 62; however, the slot may be formed elsewhere on clamp 36 or cable block 46 may be otherwise removably attached to the pole clamp 36, for example, by using a hook and eye, strips of "VELCRO®" tape, or other interconnecting devices located between the lower surface of the pole clamp 36 and the upper surface of the cable block 46. In other alternative embodiments, for example as shown in FIG. 5, the bracket 34 may contain a slot 81 that is substantially identical to the slot 62 of FIG. 3, and the cable block 46 may be slid into and supported in the slot 81 of the bracket 34. Therefore, the whole cable system 20 may be moved by simply disconnecting the bracket 34 from the mount 36.

In still further alternative embodiments, instead of being removably attached, the cable block 46 may be made or molded into and be a part of either the pole clamp 36 or the bracket 34. Alternatively, the bracket 34 may be permanently connected or made a part of the mount 36.

The invention in its broadest aspects is therefore not limited to the specific details, representative image system and illustrative examples shown and described. Accordingly, departures may be made from such details without departing from the spirit or scope of applicant's general inventive concept.

What is claimed is:

1. A medical cable system comprising:
a plurality of device cables, each having a distal end adapted to be in electrical communication with a medical sensing device and a proximal end;
a main cable having a first end electrically connected to the proximal ends of the plurality of device cables, the main cable having a second end adapted to be electrically connected to a monitor;
a furcation block supporting the proximal ends of the plurality of device cables and the first end of the main cable, the proximal ends of the plurality of the device cables and the first end of the main cable being permanently joined together in the furcation block, the permanent connection between the device cables and the main cable eliminating the need for electrical connectors connecting the device cables to the main cable, thereby improving the electrical reliability of signals being conducted by the device cables and the main cable while reducing size and cost of the furcation block;
a mount adapted to be attached to a structure;
a first coupling element on the mount; and
a cooperative coupling element on the furcation block coupled manually and without tools with the first coupling element to releasably support the furcation block on the mount, thereby permitting the furcation block to be manually and without tools quickly removed from the mount.

2. The medical system of claim 1 wherein one of the cooperative coupling elements is a slot in the mount having a shape corresponding to a shape of the furcation block to permit the furcation block to slide in the slot and be supported by the mount.

3. The medical cable system of claim 2 wherein the slot in the mount is a generally T-shaped slot and a cross-sectional profile of the furcation block is a generally T-shaped profile.

4. The medical cable system of claim 2 wherein the furcation block has an outer surface made of a pliable material providing a relatively high friction interface between the furcation block and the slot to more firmly secure the first furcation block to the mount.

5. The medical cable system of claim 1 wherein the distal ends of the plurality of device cables terminate into electrical connectors and the mount further includes a plurality of storage compartments receiving and temporarily supporting the connectors on the mount whereby placing the electrical connectors on the distal end of the device cables in the storage compartments protects the electrical connectors from contamination and damage.

6. The medical cable system of claim 5 wherein the plurality of storage compartments is a plurality of cavities formed in one end of the mount.

7. The medical cable system of claim 6 wherein the plurality of cavities are open through a lower side of the mount.

8. The medical cable system of claim 7 wherein the plurality of cavities are covered by an upper side of the mount.

9. The medical cable system of claim 1 further comprising:
a plurality of monitor cables, each of the monitor cables having a distal end adapted to be connected to the monitor and a proximal end connected to the second end of the main cable; and
a second furcation block supporting the proximal ends of the monitor cables and the second end of the main cable.

10. A medical cable system comprising:
a plurality of device cables, each having a distal end adapted to be in electrical communication with a medical sensing device and a proximal end;
a main cable having a first end electrically connected to the proximal ends of the plurality of device cables, the main cable having a second end adapted to be electrically connected to a monitor;
a furcation block supporting the proximal ends of the plurality of device cables and the first end of the main cable;
a mount adapted to be attached to a structure;
a first coupling element on the mount; and
a cooperative coupling element on the furcation block coupled manually and without tools with the first coupling element to releasably support the furcation block on the mount, thereby permitting the furcation block to be manually and without tools quickly removed from the mount,
the first coupling element is a slot in the mount having a shape corresponding to a shape of the furcation block to permit the furcation block to slide in the slot and be supported by the mount, and the furcation block having an outer surface made of a pliable material providing a relatively high friction interface between the furcation block and the slot to more firmly secure the furcation block to the mount.

11. A medical cable system providing a plurality of device cables connected to a plurality of medical sensors for measuring physical conditions of a patient, the medical cable system further providing a single cable for electrically connecting the plurality of device cables with a monitor providing a display of the physical conditions being monitored, the medical cable system further comprising:
a mount adapted to be attached to a structure in the proximity of the patient, the mount supporting the plurality of medical sensors;
a first coupling element on the mount;
a furcation block connected between the plurality of device cables and the single cable, the furcation block having thereon a second coupling element being manually and without tools coupled to the first coupling element to support the furcation block on the mount, thereby permitting the furcation block to be manually and without tools quickly removed from the mount for transportation of the device cables, the furcation block and the single cable; and
proximal ends of the plurality of the device cables and a first end of the single cable being permanently joined together in the furcation block, the permanent connection between the device cables and the single cable eliminating the need for electrical connectors connecting the device cables to the single cable, thereby improving the electrical reliability of signals being conducted by the device cables and the single cable while reducing size and cost of the furcation block.

12. The medical cable system of claim 11 wherein the first coupling component is a slot in the mount and the second coupling component is a cross-sectional profile of the furcation block that permits the furcation block to slide into the slot, thereby attaching the furcation block to the mount.

13. A medical cable system for electrically interconnecting a plurality of sensors measuring physical conditions of a patient with a monitor providing a display of the physical conditions being monitored, the medical cable system comprising:

a mount adapted to be attached to a structure;

a furcation block having a plurality of conductors adapted to be connected to respective ones of the plurality of sensors, the furcation block being removably attachable to the mount;

a main cable having
a first end supported by the furcation block and electrically connected to the plurality of conductors, and
a second end adapted to be electrically connected to the monitor; and cooperative coupling elements located on the mount and the furcation block for releasably coupling the furcation block and the mount together, the coupling element on the furcation block having a surface made of a pliable material providing a relatively high friction interface with a surface on the mount to more firmly secure the furcation block with the mount.

14. A medical cable system comprising:

a furcation block having a first mechanical coupling element;

a plurality of device cables, each having a distal end adapted to be electrically connected to a medical sensing device and a proximal end supported by the furcation block;

a main cable having a first end supported by the furcation block and electrically connected to the device cable proximal ends, the main cable having a second end adapted to be electrically connected to a monitor, the proximal ends of the plurality of the device cables and the first end of the main cable being permanently joined together in the furcation block, the permanent connection between the device cables and the main cable eliminating the need for electrical connectors connecting the device cables to the main cable, thereby improving the electrical reliability of signals being conducted by the device cables and the main cable while reducing size and cost of the furcation block; and a pole mount adapted to be attached to a pole, the pole mount supporting the medical sensing device and including a second mechanical coupling element coupling with the first mechanical coupling element of the furcation block to releasably hold the furcation block to the pole mount.

15. A medical cable system for electrically interconnecting a plurality of sensors measuring physical conditions of a patient with a monitor providing a display of the physical conditions being monitored, the medical cable system comprising:

a mount adapted to be attached onto a structure in the proximity of the patient;

a plurality of device cables, each of the device cables having a distal end, adapted to be connected to one of the sensors, and a proximal end;

a main cable having a first end, electrically connected to the proximal ends of the plurality of device cables, and a second end;

a first furcation block attached to the proximal end of each of the plurality of device cables and the first end of the main cable, the first furcation block being attached to the mount;

a plurality of monitor cables, each of the monitor cables having a distal end, adapted to be connected to the monitor, and a proximal end; and a second furcation block attached to the proximal end of each of the plurality of monitor cables and the second end of the main cable.

* * * * *